(12) United States Patent
Kim

(10) Patent No.: US 10,492,824 B2
(45) Date of Patent: Dec. 3, 2019

(54) LAPAROSCOPIC PORT PERFORATION AND CLOSURE DEVICE

(71) Applicant: Ki Seong Kim, Gyeonggi-do (KR)

(72) Inventor: Ki Seong Kim, Gyeonggi-do (KR)

(73) Assignee: Ki Seong Kim, Gyeonggi-do (KR)

( * ) Notice: Subject to any disclaimer, the term of this patent is extended or adjusted under 35 U.S.C. 154(b) by 0 days.

(21) Appl. No.: 15/555,395

(22) PCT Filed: Sep. 8, 2016

(86) PCT No.: PCT/KR2016/010069
§ 371 (c)(1),
(2) Date: Sep. 1, 2017

(87) PCT Pub. No.: WO2018/026050
PCT Pub. Date: Feb. 8, 2018

(65) Prior Publication Data
US 2019/0142454 A1    May 16, 2019

(30) Foreign Application Priority Data

Aug. 5, 2016 (KR) .................. 10-2016-0100005

(51) Int. Cl.
*A61B 17/34* (2006.01)
*A61B 17/04* (2006.01)

(52) U.S. Cl.
CPC .......... *A61B 17/3417* (2013.01); *A61B 17/04* (2013.01); *A61B 17/3403* (2013.01); *A61B 2017/348* (2013.01); *A61B 2017/3454* (2013.01)

(58) Field of Classification Search
CPC . A61B 17/0057; A61B 17/04; A61B 17/0401; A61B 17/0469; A61B 17/34; A61B 17/3403; A61B 17/3417; A61B 17/3421; A61B 17/3445; A61B 17/3454; A61B 17/3468; A61B 17/3478; A61B 17/348; A61B 2017/00637;
(Continued)

(56) References Cited

U.S. PATENT DOCUMENTS

| 2005/0065543 A1* | 3/2005 | Kahle ................ A61B 17/3417 606/190 |
| 2014/0163323 A1* | 6/2014 | Mohajer-Shojaee ......................... A61B 17/0057 600/204 |
| 2015/0216514 A1 | 8/2015 | Weisbrod et al. |

FOREIGN PATENT DOCUMENTS

| KR | 101132070 | 4/2012 |
| WO | WO 2011/128392 | 10/2011 |

* cited by examiner

*Primary Examiner* — Robert A Lynch
(74) *Attorney, Agent, or Firm* — IP & T Group LLP

(57) ABSTRACT

Disclosed is a laparoscopic port perforation and closure device configured such that a perforation device for perforating a laparoscopic port on a patient's body, a trocar for maintaining the port and allowing various surgical tools to be introduced therethrough, and a closure device for closing the port are selectively used in a single trocar assembly. The device includes: a trocar (4) configured such that a handle is coupled to a first end of a sleeve formed in a tubular shape for being introduced into a perforated port; a penetrating tip (37) with an end tip thereof being exposed outside a second end of the sleeve by sequentially penetrating the handle and the sleeve of the trocar, and configured to enter an abdominal cavity by opening a port; and a combined perforation/closure assembly (3) closing the opened port by replacing the penetrating tip (37) with a closure cartridge (36).

8 Claims, 14 Drawing Sheets

(58) Field of Classification Search
CPC .. A61B 2017/00663; A61B 2017/3454; A61B 2017/346
See application file for complete search history.

LAPAROSCOPIC PORT PERFORATION AND CLOSURE DEVICE

This application is a national stage application of PCT/KR2016/010069 filed on Sep. 8, 2016, which claims priority of Korean patent application number 10-2016-0100005filed on Aug. 5, 2016. The disclosure of each of the foregoing applications is incorporated herein by reference in its entirety.

TECHNICAL FIELD

The present invention relates generally to a laparoscopic port perforation and closure device. More particularly, the present invention relates to a laparoscopic port perforation and closure device configured such that a perforation device for perforating a laparoscopic port on a patient's body, a trocar for maintaining the port and allowing various surgical tools to be introduced therethrough, and a closure device for closing the port are selectively used in a single trocar assembly.

BACKGROUND ART

In general, laparoscopic surgery, unlike conventional open surgical procedures, refers to a surgical technique where four to six incisions about 0.5~1.2 cm in size are made in the patient's abdomen, and trocars, which have a diameter of 0.5~1.2 cm and are 15~16 cm long, are placed through these incisions. A light source, a camera, and surgical instruments are then introduced into the abdomen through the trocars. The surgeon performs the procedure, watching a television monitor to which the camera transmits an image of the organs inside the abdomen.

For laparoscopic surgery, after a plurality of trocars is placed into a patient's abdomen, carbon dioxide gas is used to inflate the abdomen through one of the trocars in order to give the surgical space to work. The endoscope and surgical instruments are then introduced through other trocars. The surgeon performs a surgery for the affected area, monitoring the surgical site.

After the procedure, in order to close the incisions, a trocar site closure tool is used. The trocar site closure tool is configured such that the incisions are closed by stitching while the needle is held by the forceps that are placed into the abdominal cavity through the trocar. After closing the incisions, in order to prevent the stitches from being untied, opposite ends of the surgical suture are pulled out of the patient's body through the trocar, and the knots are tied outside the patient's body. After tying the knots, the knots are formed into the abdominal cavity by pushing the knots using a compressor.

After the surgical site inside the abdominal cavity is treated, the trocar is removed and the port is closed.

Port closure can be done by direct suturing or by using a closure device.

According to a conventional art, the perforation of the port by the trocar secures the operative pathway, and the closure of the port by the closure device is performed by using a separate device.

As shown in FIG. 1, a trocar is used to form a surgical port site, the trocar 10 includes: a tubular sleeve 14 with a penetrating tip 16 penetrating therethrough; and a handle 12 provided at an upper portion of the sleeve, wherein an end of the penetrating tip 16 is constituted by a pointed end 16a to penetrate through subcutaneous tissue of an abdominal cavity, whereby after perforating a port, the penetrating tip is removed, various surgical tools are introduced through the trocar 10 to perform surgery.

After the surgery, the trocar 10 is removed and the port is closed by using a closure device as shown in FIG. 2.

The closure device shown in FIG. 2 is well known to those skilled in the art, and the use thereof is gradually increasing since it provides safety allowing rapid closure of the port without failure.

The closure device is also known as a fascial closure device.

The fascial closure device, which is in a tube shape for being introduced into a port site, includes: a tubular body 21 formed with guide groove 22 that face each other and guide insertion of a needle 23; and a pair of wings 25 being mounted to a lower portion of the tubular body, and being opened and closed using cam method, wherein each of the wings is provided with a silicon pad 26 at a location where the needle 23 penetrates through, and the wings 25 are configured to be opened by rotating an operating stick 24 and configured to be closed by reversely rotating the operating stick 4.

The inventor of the present invention filed the document a laparoscopic port site closure device, which has a new structure that improves disadvantages of a conventional closure device, and it is registered as Korean Patent No. 1594082.

According to the above document of the inventor, the laparoscopic port site closure device is configured such that a cartridge receiving a surgical suture therein is provided at a fore-end of a needle guide for port site closure; the surgical suture is caught in a needle tip that is pierced through a body tissue by being guided by the needle guide; and when the needle is withdrawn, the surgical suture is pulled out along a path through which the needle is pierced into the tissue, and the surgical suture is tied outside a patient's body, thereby being capable of closing a laparoscopic port site. The closure device includes: a tubular body provided with needle guides that face each other and guide insertion of a needle; wings mounted to a lower portion of the tubular body such that the wings are opened and closed through a cam method; and an operating stick penetrating through the tubular body to operate the wings by being rotated to push and open the wings and to pull and close the wings by being rotated reversely, wherein a replaceable cartridge is provided on a lower end of the tubular body to be detachably combined with the operating stick, and the cartridge is provided with the wings capable of being opened by operating the operating stick, and provided with a compartment for receiving surgical suture therein, whereby opposites ends of the surgical suture in the compartment are threaded through the wings such that the ends of the surgical suture are pulled out of a patient's body by being caught by a suture slot of a needle that is pierced into the patient's body from outside.

According to the inventor's document of the prior patent, the cartridge receiving a surgical suture therein is replaceable, whereby the port site can be easily closed without failure, and the closure device is reusable by replacing the cartridge receiving the surgical suture therein. However, since the conventional closure device including the prior patent is limited to a closure device that simply closes an opened port, port opening and port closure are performed through different devices.

Since opening and closure are performed by different devices, when the fascial closure device (the closure device) is introduced through the port site after removing the trocar to after surgery, the gas injected inside the abdominal cavity overly escapes, whereby the surgical space narrows so it is difficult to perform a follow-up treatment, the operation time may be long due to removal of the trocar and the replacement of the fascial closure device, which is an obstacle to the patient's prognosis.

DISCLOSURE

Technical Problem

Accordingly, the present invention has been made to solve the above problem occurring in the related art that a function of the trocar and a function of the closure device are divided.

The present invention is intended to propose a laparoscopic port perforation and closure device, in which a perforation/closure assembly being introduced in the abdominal cavity through a trocar sleeve is provided, thereby serving as both perforation of a peritoneum and closure of the opened port.

The present invention is intended to propose a laparoscopic port perforation and closure device, in which a perforation/closure assembly replaced with a closure cartridge is inserted into a trocar sleeve without removing a trocar to suture, such that the reverse flow of the gas injected inside the abdominal cavity is minimized, whereby it is advantageous to stably secure the surgical space and suturing time may be shortened.

The present invention is intended to propose a laparoscopic port perforation and closure device, in which an end of the body of the laparoscopic port perforation and closure device is provided with a detachable cartridge, such that the cartridge is replaceable after being repeatedly used, whereby it is easy to use and there is no risk of infection because it is discarded after reuse for the same patient.

Technical Solution

In order to achieve the above object, according to one aspect of the present invention, there is provided a laparoscopic port site closure device configured as follows.

The perforation and closure device includes: a trocar configured such that a handle is coupled to a first end of a sleeve formed in a tubular shape for being introduced into a perforated port; a perforation and closure means hooked to the handle of the trocar and configured such that an end tip thereof enters an abdominal cavity by sequentially penetrating the handle and the sleeve of the trocar.

The perforation and closure means may include: a hooked to the handle of the trocar; a bisected cover rod longitudinally extending from the handle; a holder provided therein and configured to rotate within a limited angle range in the cover rod and move up and down within a limited distance; a closure cartridge inserted into and locked to a lower portion of the cover rod; and a penetrating tip inserted into and locked to the lower portion of the cover rod or inserted into the lower portion of the cover rod and locked thereto by the holder, whereby the closure cartridge and the penetrating tip are selectively coupled to the perforation and closure device and are replaceable.

The cover rod may be formed with helical needle guide grooves at an outer circumferential surface thereof.

The penetrating tip may be provided with a pointed end to be coupled to an end of the cover rod, and an outer diameter of the penetrating tip may correspond to an outer diameter of the cover rod.

The closure cartridge may include: wings coupled to an end of the cover rod and controlled by the holder to be opened and closed; and a compartment receiving a surgical suture therein, whereby opposite ends of the surgical suture are threaded through the wings such that the ends of the surgical suture are pulled out of a patient's body by being caught by a needle that is pierced into a patient's body from outside.

Advantageous Effects

According to the present invention having the above-described characteristics, the port opening function of trocar and the port closing function of the closure device are conventionally realized by the respective devices, but it is possible to realize the port opening and the port closing through a single device.

The present invention is advantageous in that it is possible to serve as both perforation of a peritoneum and closure of the opened port after surgery through a perforation/closure assembly that is firmly coupled and easily replaceable.

The present invention is further advantageous in that it is possible to solve the problem that the gas injected inside the abdominal cavity flows out through the port when a separate closure device is inserted to close the port after removing the trocar.

In other words, since the present invention is configured such that a perforation/closure assembly replaced with a closure cartridge is inserted into a trocar sleeve without removing a trocar to suture, the reverse flow of the gas injected inside the abdominal cavity is minimized, whereby it is advantageous to secure the surgical space constantly and suturing time may be shortened.

The present invention is further advantageous in that since an end of the body of the laparoscopic port perforation and closure device is provided with a detachable cartridge, the cartridge is replaceable after being repeatedly used, whereby it is easy to use and there is no risk of infection because it is discarded after reuse for the same patient.

BEST MODE

Figure 1:
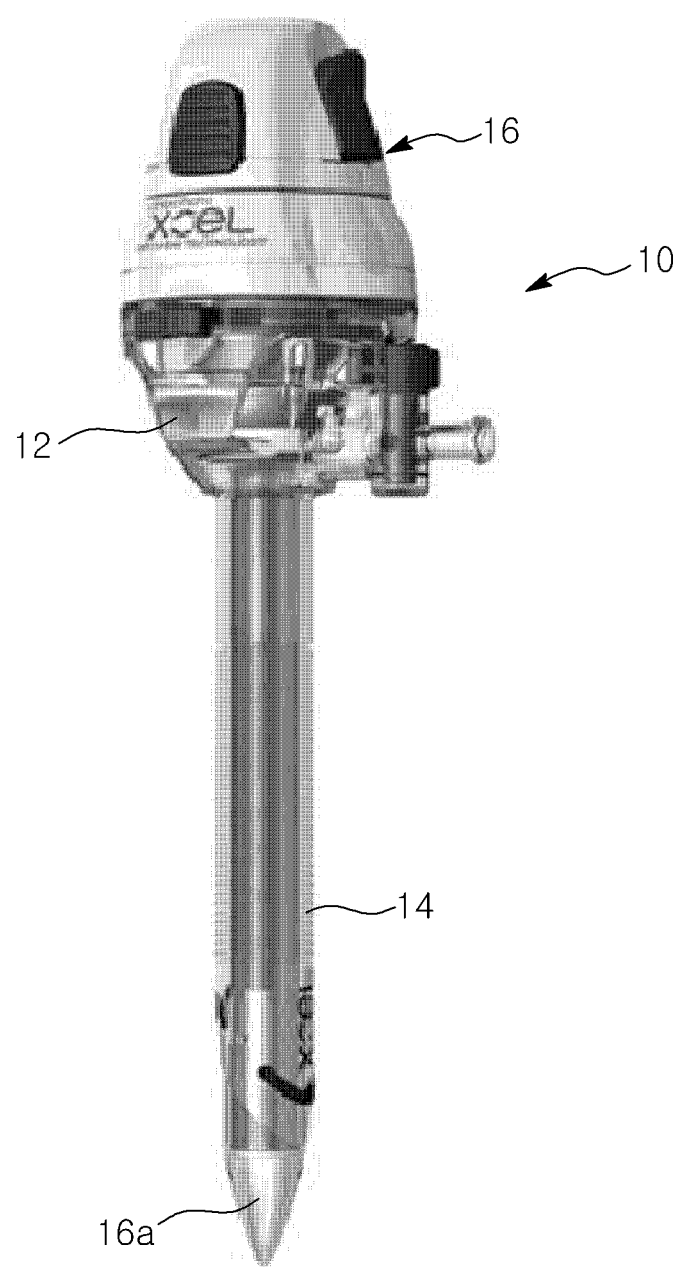
FIG. 1 exemplarily shows an outside view of a trocar as a conventional laparoscopic port site perforation device.
Figure 2:
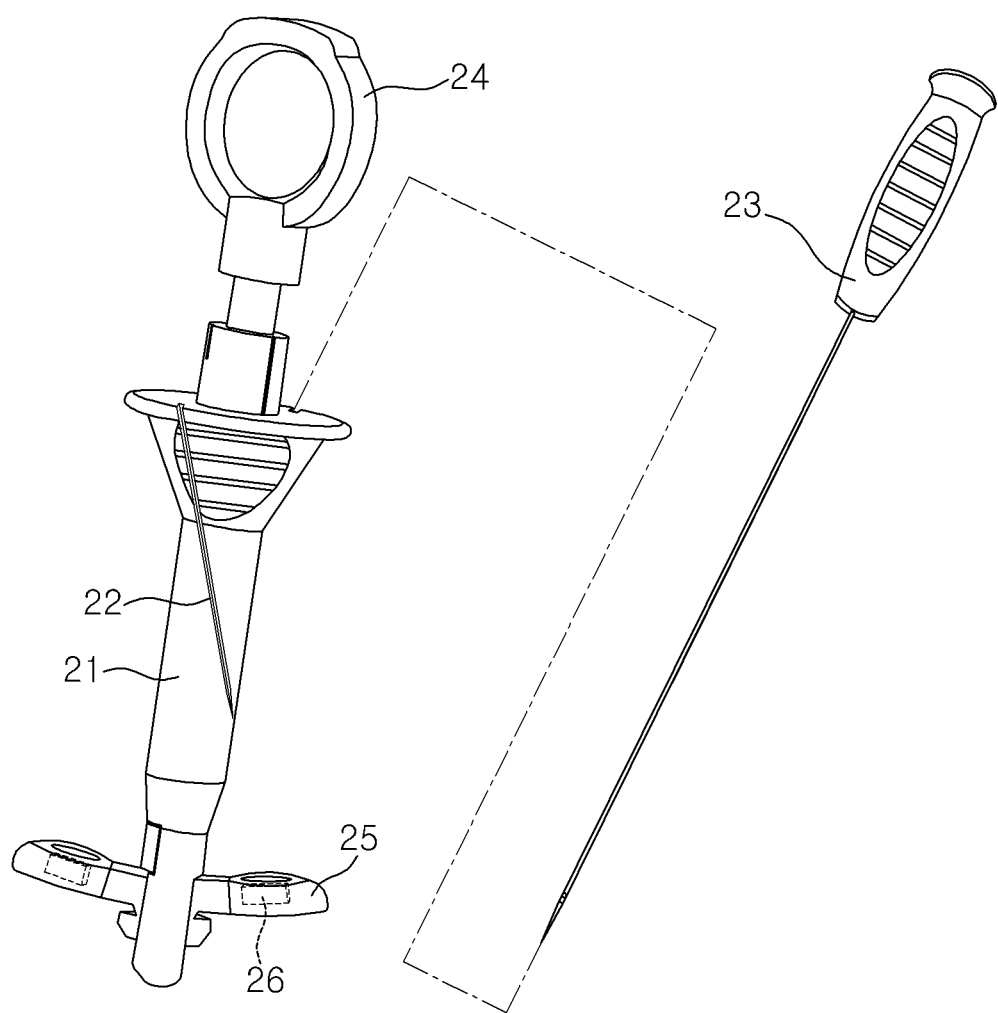
FIG. 2 exemplarily shows an outside view of a closure tool as a laparoscopic port site closure device.
Figure 3:
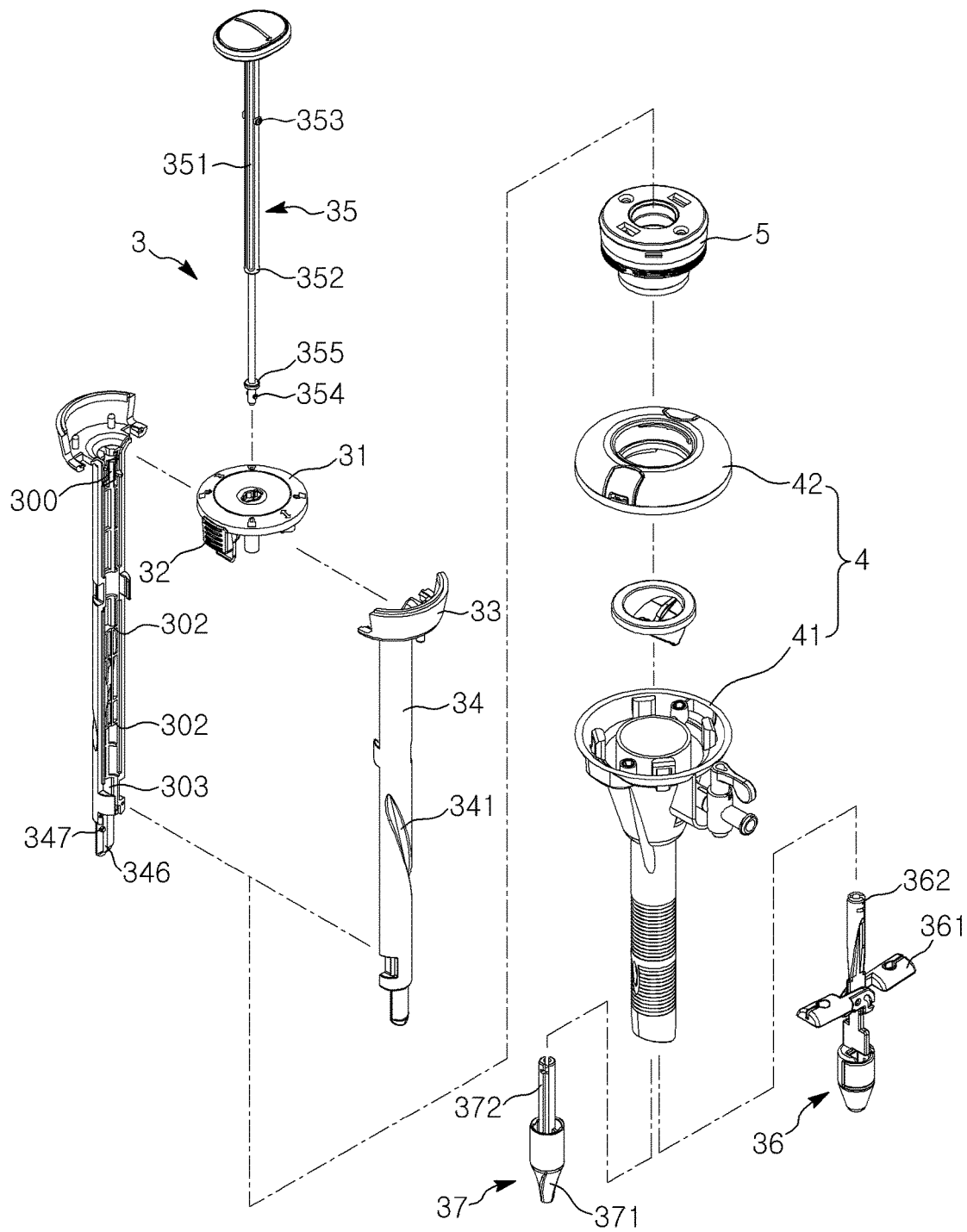
FIG. 3 shows an exploded perspective view of a laparoscopic port perforation and closure device including a perforation/closure assembly of the present invention.
Figure 4:
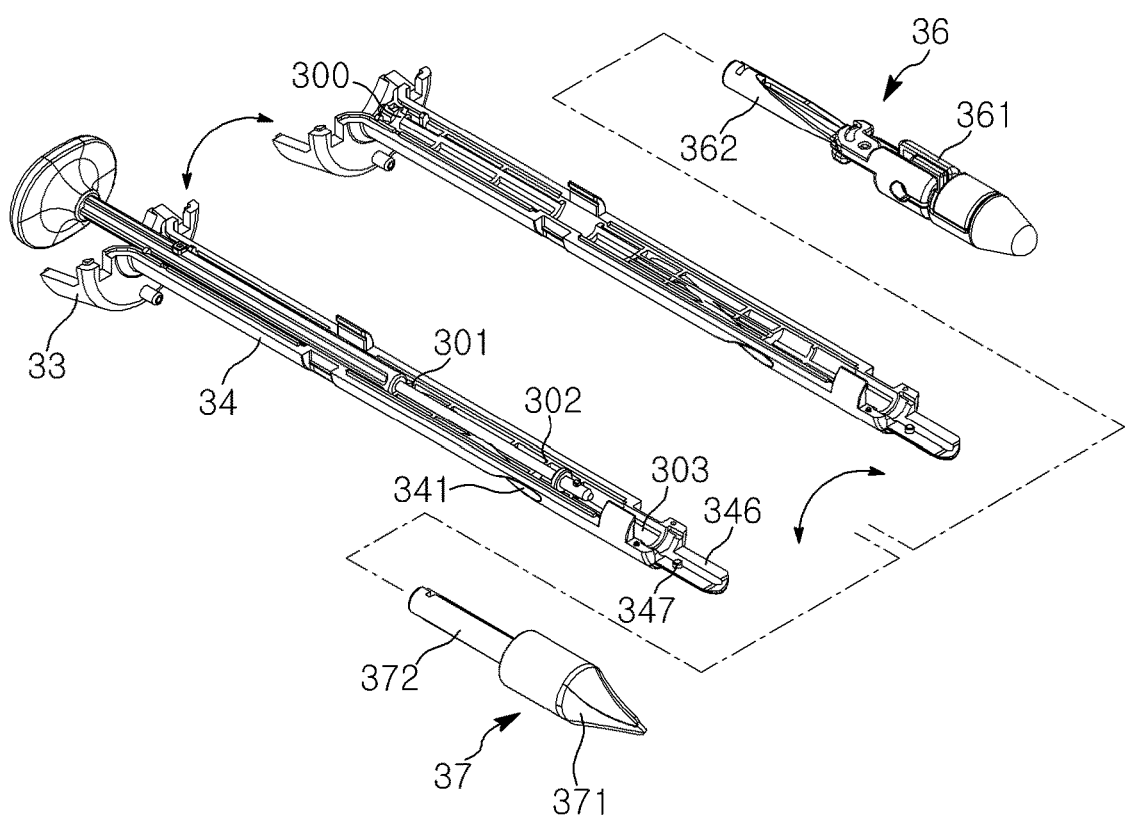
FIG. 4 shows a schematic view of essential portions of the perforation/closure assembly of the present invention.
Figure 5:
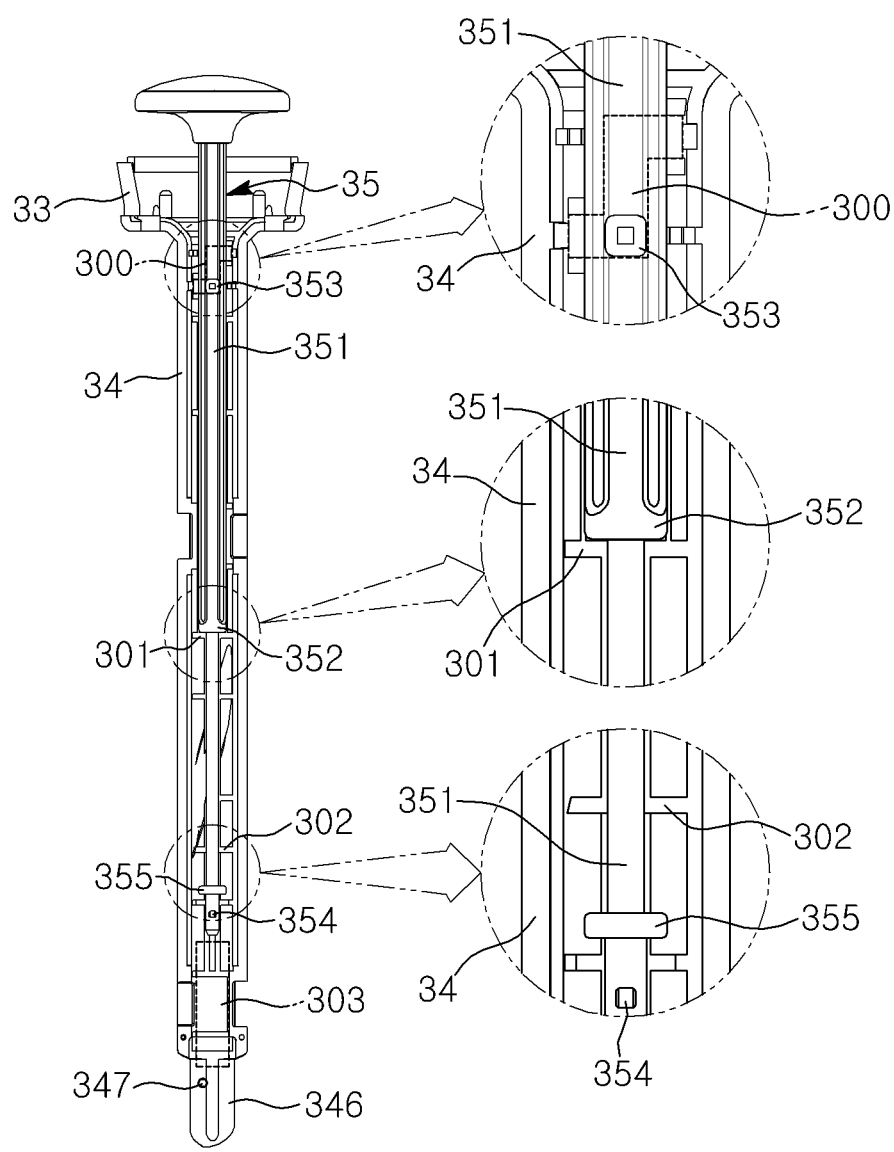
FIG. 5 shows a plane view of the perforation/closure assembly shown in FIG. 4.
Figure 6:
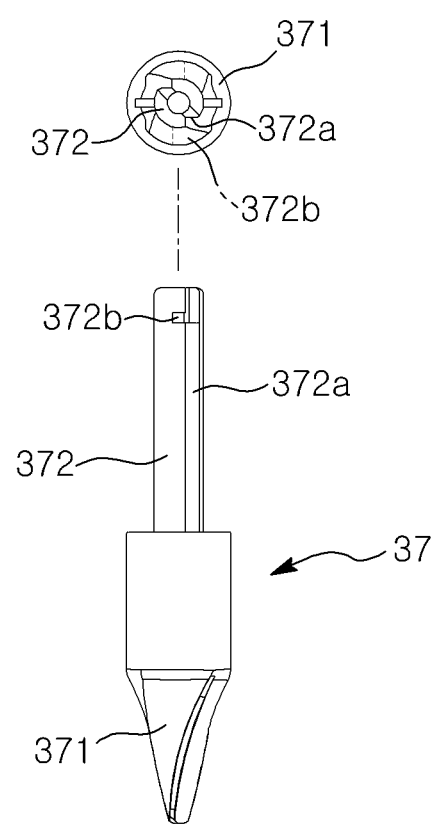
FIG. 6 shows a plane state view and a front state view of a penetrating tip of the present invention.
Figure 7:
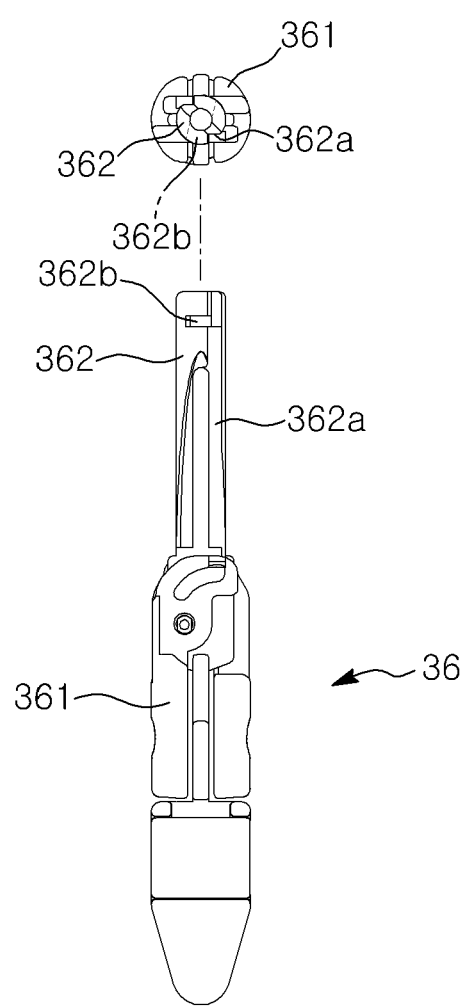
FIG. 7 shows a plane state view and a front state view of a closure cartridge of the present invention.
Figure 8:
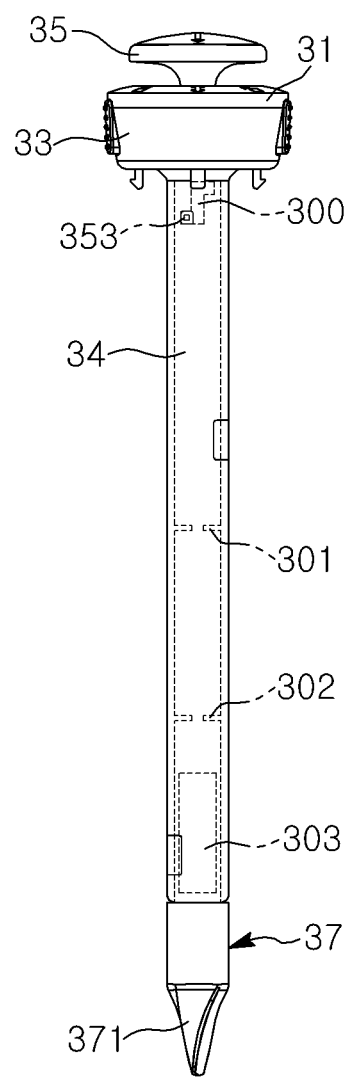
FIG. 8 shows an operational state view of essential portions showings the perforation/closure assembly of the present invention.

Hereinbelow, a detailed configuration and operation of the present invention will be described with reference to the accompanying drawings.

In a trocar configured such that a handle is coupled to a first end of a sleeve formed in a tubular shape for being introduced into a perforated port, a penetrating tip is configured such that an end tip thereof is exposed outside a second end of the sleeve by sequentially penetrating the handle and the sleeve of the trocar to enter an abdominal cavity, and a perforation and closure means is configured to be coupled to a closure cartridge by removing the penetrating tip and coupled to the handle of the trocar by a one-touch hook.

The perforation and closure means is constituted by a combined perforation/closure assembly 3 detachably mounted to the trocar and configured such that the penetrating tip is coupled to an end thereof when opening (perforating) a port, and the closure cartridge is coupled to the end thereof when closing (suturing) the port.

The perforation/closure assembly 3 includes: a handle cover 31 coupled to the handle of the trocar by a one-touch hook 32; a bisected cover rod 34 longitudinally extending from the handle 33; a holder 35 provided therein and configured to rotate within a limited angle range in the cover rod 34 and move up and down within a limited distance; a closure cartridge 36 inserted into and locked to a lower portion of the cover rod 34; and a penetrating tip 37 inserted into and locked to the lower portion of the cover rod 34 or inserted into the lower portion of the cover rod 34 and locked thereto by the holder 35, whereby the closure cartridge 36 and the penetrating tip 37 are selectively coupled to the perforation and closure device and are replaceable.

The cover rod 34 is formed with a helical needle guide groove 341 at an outer circumferential surface thereof, and a plurality of the cover rods 34 is disposed to face each other and coupled to the handle cover 31 provided with the one-touch hook 32 therein.

The cover rod 34 is configured such that upper and lower portions thereof are respectively provided with a coupling hook 342 and a coupling groove 343 to face each other, a plurality of the cover rods is coupled to face each other, and the cover rod 34 is provided with the holder 35 therein.

The cover rod 34 is provided with a crank-shaped groove 345 at an inner upper portion thereof to form a lock/unlock constraint part 300, is provided with a step at an inner middle portion thereof to form a downward-motion constraint part 301, is provided with a step at an inner lower portion thereof to form a upward-motion constraint part 302, and is provided with a protruding piece 346 having an inner protrusion 347 at a lowermost portion thereof, thereby being formed in a tubular shape to form a neck entrance 303 at a lower end thereof when the cover rods are assembled to face each other.

The holder 35 includes: a holding rod 351 provided with a step 352 under the handle with an upper diameter thereof large and a lower diameter thereof small; upper and lower protruding portions 353 and 354 provided at upper and lower portions of the holding rod; and a stopper 355 provided to protrude in a disc shape at a location right above the lower protruding portion.

The upper protruding portion 353 of the holding rod 351 is engaged with a crank-shaped groove 345 of the cover rod 34, the step 352 is disposed at an upper portion of a downward-motion constraint part 301 to constrain downward-motion, the stopper 355 is disposed at a lower portion of an upward-motion constraint part 302 to constrain upward-motion, and an up-and-down moving distance of the holding rod 351 is constrained by the crank-shaped groove 345 and the upward-motion and downward-motion constraint parts 302 and 301.

The crank-shaped groove 345 constitutes a lock/unlock constraint part 300 horizontally rotating at a location where the holding rod 351 moves up or down for locking and unlocking the same.

The penetrating tip 37 is provided with a pointed end 371 and a neck 372 longitudinally extending upward at a center thereof to be detachably coupled to an end of the cover rod 34, and it is preferred that an outer diameter of the penetrating tip correspond to an outer diameter of the cover rod.

The closure cartridge 36 includes: wings 361 detachably coupled to an end of the cover rod 34 by inserting a neck 362 thereinto and controlled by the holder 35 to be opened and closed; and a compartment receiving a surgical suture therein, whereby opposite ends of the surgical suture are threaded through the wings 361 such that the ends of the surgical suture are pulled out of a patient's body by being caught by a needle that is pierced into a patient's body from outside.

The closure cartridge 36 is already known to those skilled in the art by the inventor's prior patent, so the detailed description of the configuration thereof will be skipped, and the operation process thereof will be described in detail hereinafter.

The present invention may be realized by modifying the structure of the replaceable penetrating tip 37, and by modifying the assembly structure of the cover rods 34 facing each other.

Figure 13:
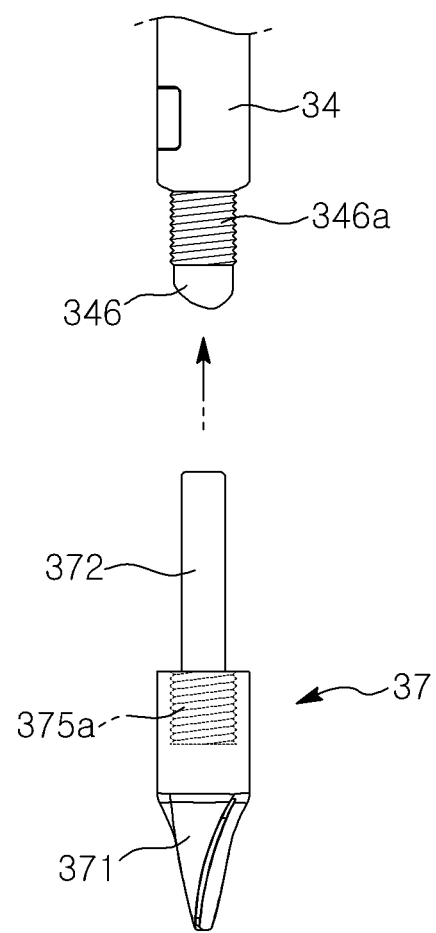
FIGS. 13 to 14 show schematic views of modification of penetrating tip of the present invention.

The penetrating tip 37 may be configured such that a pointed end 371 is provided with inner threads 375 at an inside thereof and a protruding piece 346 of the cover rod 34 is provided with outer threads 346a, so as to be fixedly inserted into a lower portion of the cover rod 34 by the inner threads 375 being engaged with the outer threads 346a (see FIG. 13).

Figure 14:
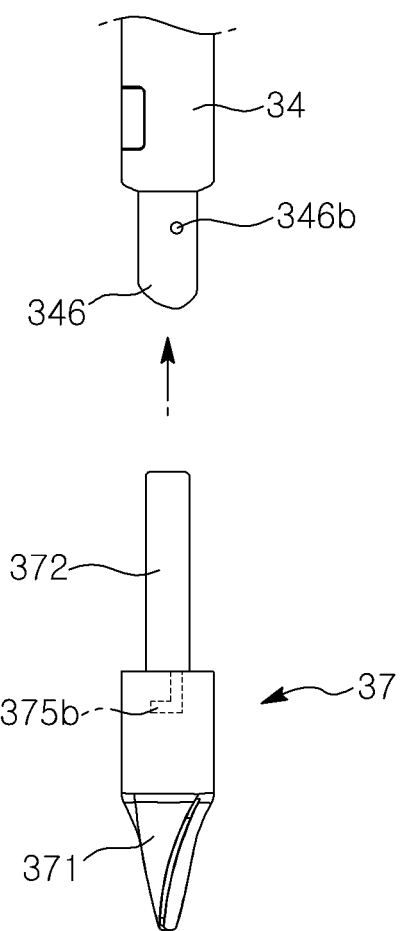

Further, the penetrating tip 37 may be configured such that a pointed end 371 is provided with an inner groove 375b at an inside thereof and a protruding piece 346 of the cover rod 34 is provided with an outer protrusion 346b, so as to be fixedly inserted into a lower portion of the cover rod by the inner groove being engaged with the outer protrusion (see FIG. 14).

Reference will be made in greater detail to the present invention configured as described above.

As known to those skilled in the art, the laparoscopic port perforation and closure device of the present invention serves as a trocar that opens and maintains an operative pathway mainly through a patient's peritoneum.

The laparoscopic port perforation and closure device of the present invention opens a surgical port and closes the opened port.

Figure 9A:
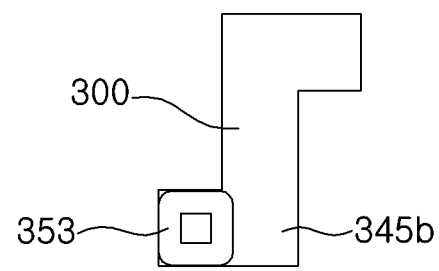
FIGS. 9A-9B shows operational views of a state where the penetrating tip is detached from and coupled to the device by a lock/unlock constraint part of FIG. 8.
Figure 9B:
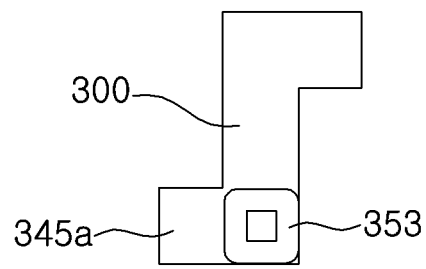
Figure 10A:
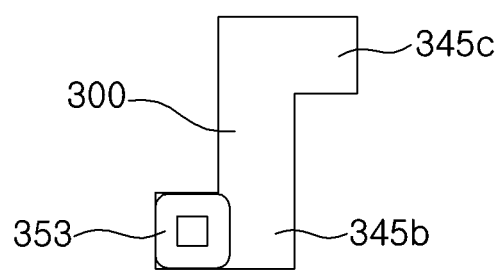
FIGS. 10A-10D shows operational views of a state where the closure cartridge is detached from and coupled to the device by the lock/unlock constraint part of FIG. 8.
Figure 10B:
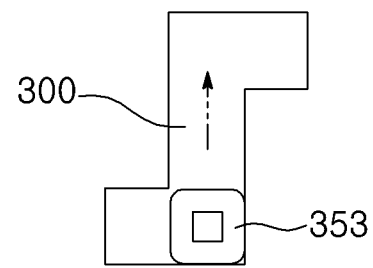
Figure 10C:
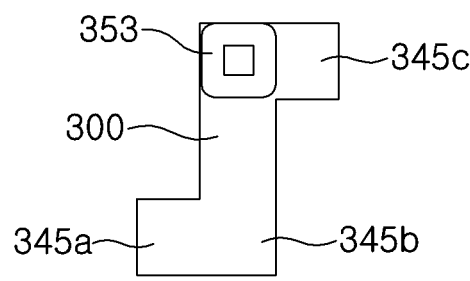
Figure 10D:
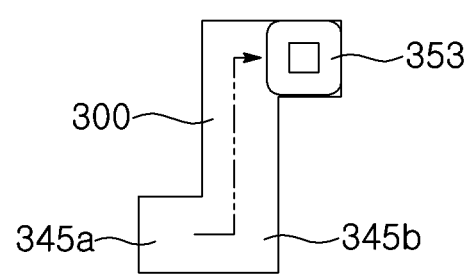
Figure 11:
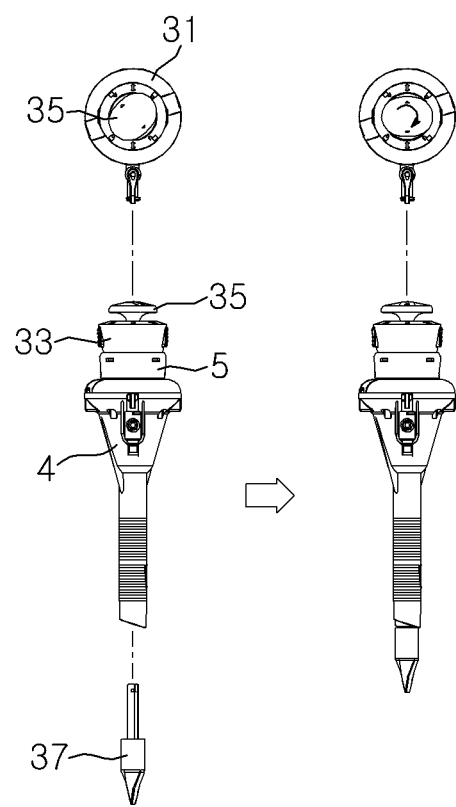
FIG. 11 shows an operational view of a state where the penetrating tip of the present invention is detached from and coupled to the device.

Firstly, reference will be made to the opening procedure shown in FIGS. 9 and 11.

To open the port, the penetrating tip 37 is locked to the lowermost portion of the cover rod 34 of the perforation/closure assembly 3 of the present invention.

The penetrating tip 37 is firmly locked in such a manner that the neck 372 having a linear guide groove 372a and a locking groove 372b is inserted into the neck entrance 303 of the lower portion of the cover rod 34, and the holder 35 is rotated in a direction such that the lower protruding portion 354 of the holder is engaged with the locking groove 372b of the penetrating tip 37.

The reason why the protrusion 347 of the protruding piece 346 is inserted at a predetermined angle while guiding the guide groove 372a of the penetrating tip 37 when the neck 372 enters is to align the lower protruding portion 354 of the holding rod 351 and the locking groove 372b of the penetrating tip 37 to be engaged with each other, and this insertion induction action is also applied when the closure cartridge 36 is coupled and separated.

When the neck 372 of the penetrating tip 37 is inserted deeply into the neck entrance 303 and the holding rod 351 is rotated, the lower protruding portion 354 is engaged with the locking groove 372b and at the same time, the upper protruding portion 353 is moved to a groove of the crank-shaped groove 345 (moved from 345a to 345b), and the penetrating tip and the end of the cover rod 34 are brought into contact with each other, whereby the upward and downward motion of the holding rod 351 is constrained by not being moved to a direction of the groove 345c and the locking of the penetrating tip 37 is completed.

When the perforation/closure assembly 3 with the penetrating tip 37 being locked thereto is coupled to the trocar 4, the one-touch hook 32 is hooked to the connector 5, whereby the preparation for inserting the trocar into the abdominal cavity is completed.

It is well known to grip and insert the perforation/closure assembly 3 coupled to the trocar 4 into the incised peritoneum by pressing the same.

After inserting the trocar into the abdominal cavity, the one-touch hook 32 is disengaged and the perforation/closure assembly 3 is removed from the trocar 4.

After that, it is also well known that surgery is performed through the trocar 4.

When the operation is completed, the penetrating tip 37 coupled to the lower portion of the removed perforation/closure assembly 3 is removed and the closure cartridge is coupled thereto for closing the port. To achieve this, the holding rod 351 is reversely rotated to the groove (from 345b to 345a) such that the lower protruding portion 354 and the locking groove 372b are disengaged from each other, whereby the penetrating tip 37 is removed by pulling it.

Figure 12:
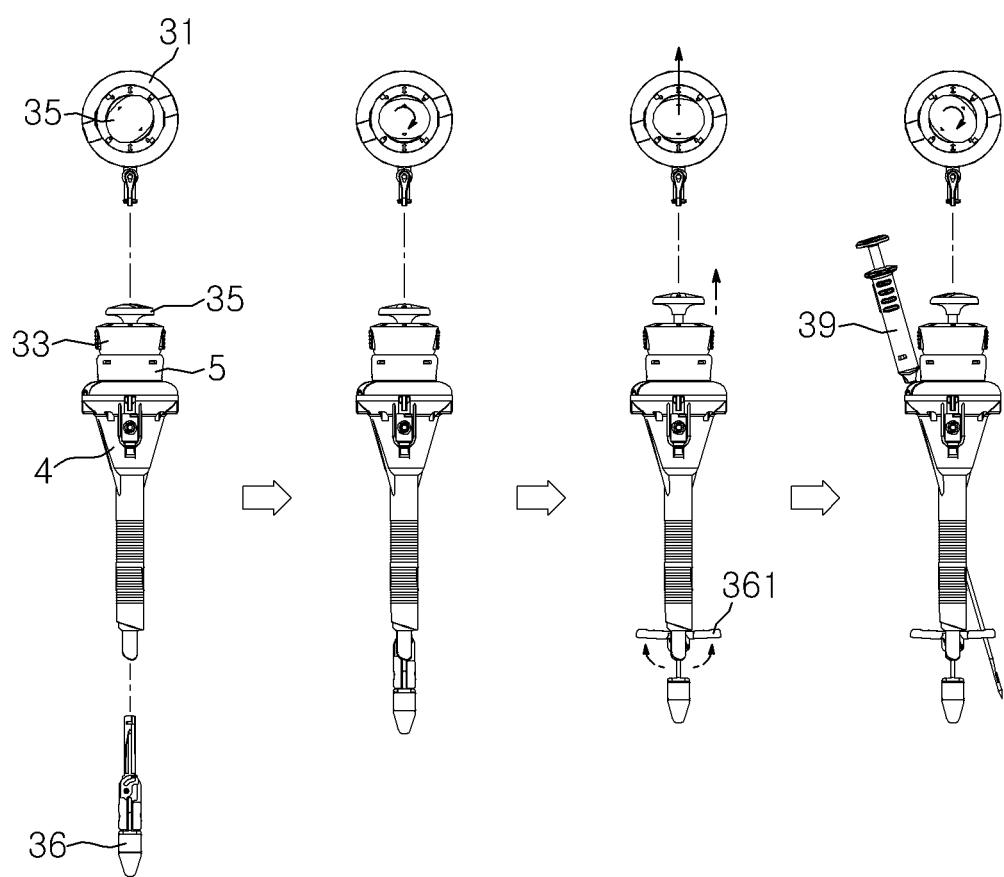
FIG. 12 shows an operational view of a state where the closure cartridge of the present invention is detached from and coupled to the device.

As shown in FIGS. 12 and 10, the neck 362 of the closure cartridge 36 is pushed into the lower portion of the perforation/closure assembly 3 with the penetrating tip removed therefrom, and is locked thereto by rotating the holding rod 351.

The perforation/closure assembly 3 with the closure cartridge 36 coupled thereto is inserted into the trocar 4 inserted through the peritoneum, and then the holding rod 351 is pulled upward, the upper protruding portion 353 is moved upward along the groove 345b of the crank-shaped groove 345. Here, as the groove of the wings 361 is guided to the protrusion 347 of the protruding piece 346, the wings 361 are opened horizontally, and when the holding rod 351 is further rotated, the upper protruding portion 353 is engaged with the groove 345c, thereby preventing the holding rod 351 from being moved downward such that the opened wings 361 is prevented from being closed.

The specific configuration and the operation of the closure cartridge 36 are already mentioned in the document of the inventor's prior patent.

Briefly, the closure cartridge 36 is configured such that the compartment thereof receives the rolled surgical suture therein, and the opposite ends of the surgical suture are threaded through the wings 361, whereby the ends of the surgical suture are pulled outside a patient's body by being caught by a needle pierced into the needle.

Accordingly, suturing is performed in such a manner that a cap of the handle 42 of the trocar 4 is opened and the suturing needle is stuck thereinto, then the needle passes through the sleeve 41 along the helical needle guide groove 341 and reaches the opened wings 361, an end of the surgical suture provided in the wings is caught by the needle 39 and pulled outside the patient's body, and from the opposite direction, the needle is stuck thereinto and the above process is repeated, the wings 361 are closed by reversely rotating the holding rod 351 such that the perforation/closure assembly 3 is removed from the sleeve 41, the surgical suture is tied to close the port.

The trocar 4 inserted through a different site is closed by the above manner. Here, the closure cartridge 36 is coupled to the device by replacing the used the closure cartridge with a new one and is inserted into the peritoneum to close the port, whereby all of the ports can be closed.

As shown in FIG. 13, in the case where the penetrating tip is configured such that the pointed end 371 is provided with the inner threads 375 at the inside thereof, and the protruding piece 346 of the cover rod 34 is provided with the outer threads 346a so as to be fixedly inserted into the lower portion of the cover rod 34 by the inner threads 375 being engaged with the outer threads 346a, the coupling and separation are performed not by the locking groove 372b but by the inner threads 375 being engaged with the outer threads 346a.

Further, as shown in FIG. 14, the penetrating tip 37 may be configured such that the pointed end 371 is provided with the inner groove 375b at the inside thereof, and the protruding piece 346 of the cover rod 34 is provided with the outer protrusion 346b, so as to be fixedly inserted into the lower portion of the cover rod by a horizontal groove of the inner groove 375b being engaged with the outer protrusion 346b.

Unlike the closure cartridge 36, the penetrating tip 37 can be adopted as long as it is firmly coupled to and easily removed from the lower end of the cover rod 34, and any structure that is convenient to use in the surgical field and cannot be easily separated during surgery can be applied, and variations thereof are not limited to a predetermined shape. It is understood by those skilled in the art that various changes and modifications may be made in the invention without departing from the spirit and scope thereof The port opening and closure described above are performed by using the perforation/closure assembly 3, wherein the penetrating tip 37 or the closure cartridge 36 is selectively coupled to the lower end thereof so that the perforation/closure assembly can be used in combination, a plurality of ports of trocars is closed by coupling the closure cartridge 36, whereby the operation time is shortened, and the number of tools for opening and closing the port is reduced, so it is economical.

DESCRIPTION OF REFERENCE CHARACTERS
OF IMPORTANT PARTS

3: perforation/closure assembly 31: handle cover
32: one-touch hook 33: handle

34: cover rod 35: holder
36: closure cartridge 37: penetrating tip
300: lock/unlock constraint part 301: downward-motion constraint part
302: upward-motion constraint part 303: neck entrance
341: needle guide groove 342: coupling hook
343: coupling groove 345: crank-shaped groove
346: protruding piece 346a: outer threads
346b: outer protrusion 347: protrusion
351: holding rod 352: step
353: upper protruding portion 354: lower protruding portion
355: stopper 361: wings
362, 372: neck 362a, 372a: guide groove
362b, 372b: locking groove 371: pointed end
375a: inner threads 375b: inner groove

The invention claimed is:

1. A laparoscopic port perforation and closure device comprising:
a trocar configured such that a handle is coupled to a first end of a sleeve formed in a tubular shape for being introduced into a perforated port;
a connector detachably coupled to an upper portion of the handle of the trocar;
a penetrating tip hooked to the connector, with an end tip thereof being exposed outside a second end of the sleeve by sequentially penetrating the handle and the sleeve of the trocar, and configured to enter an abdominal cavity by perforating a port; and
a combined perforation/closure assembly configured to close the perforated port by replacing the penetrating tip with a closure cartridge,
wherein the perforation/closure assembly includes a cover rod including a plurality of bisected cover rods each bisected cover rod longitudinally extending from a handle of the perforation/closure assembly, a holder disposed within the cover rod and configured to be rotated within a limited angle range and moved up and down within a limited distance inside the cover rod,
wherein the closure cartridge is inserted into and locked to a lower portion of the cover rod,
wherein the penetrating tip is inserted into and locked to the lower portion of the cover rod,
wherein any one of the closure cartridge and the penetrating tip is selectively coupled to the perforation and closure device, and
wherein the closure cartridge and the penetrating tip are repeatedly used by replacing the same.

2. The perforation and closure device of claim 1, wherein the cover rod is formed with a helical needle guide groove at an outer circumferential surface thereof, and is coupled to a handle cover provided with a one-touch hook therein.

3. The perforation and closure device of claim 1, wherein the cover rod is configured such that upper and lower portions thereof are respectively provided with a coupling hook and a coupling groove to face each other, the cover rod is provided with a crank-shaped groove at an inner upper portion thereof to form a lock/unlock constraint part, is provided with a step at an inner middle portion thereof to form a downward-motion constraint part, is provided with a step at an inner lower portion thereof to form a upward-motion constraint part, and is provided at a lowermost portion thereof with a protruding piece having an inner protrusion, thereby being formed in a tubular shape to form a neck entrance at a lower end thereof when the cover rods are assembled to face each other.

4. The perforation and closure device of claim 1, wherein the holder includes: a holding rod provided with a step under the handle with a large upper diameter thereof and a small lower diameter thereof; upper and lower protruding portions provided at upper and lower portions of the holding rod; and a stopper provided to protrude in a disc shape at a location right above the lower protruding portion,
the upper protruding portion of the holding rod is engaged with a crank-shaped groove of the cover rod, the step is disposed at an upper portion of a downward-motion constraint part to constrain downward-motion of the holding rod, the stopper is disposed at a lower portion of an upward-motion constraint part to constrain upward-motion of the holding rod, and an up-and-down moving distance of the holding rod is constrained by the crank-shaped groove and the upward-motion and downward-motion constraint parts, and
the crank-shaped groove constitutes a lock/unlock constraint part horizontally rotating at a location where the holding rod moves up or down for locking or unlocking the same.

5. The perforation and closure device of claim 1, wherein the penetrating tip is provided with a pointed end and a neck longitudinally extending upward at a center thereof to be detachably coupled to an end of the cover rod, and an outer diameter of the penetrating tip corresponds to an outer diameter of the cover rod.

6. The perforation and closure device of claim 1, wherein the closure cartridge includes: wings detachably coupled to an end of the cover rod by inserting a neck thereinto and controlled by the holder to be opened and closed; and a compartment receiving a surgical suture therein, whereby opposite ends of the surgical suture are threaded through the wings such that the ends of the surgical suture are pulled out of a patient's body by being caught by a needle that is pierced into a patient's body from outside.

7. The perforation and closure device of claim 1, wherein the penetrating tip is configured such that inner threads are provided at locations inside a pointed end thereof, and outer threads are provided on a protruding piece of the cover rod, so the penetrating tip is fixedly inserted into a lower portion of the cover rod by engagement of the inner threads and the outer threads.

8. The perforation and closure device of claim 1, wherein the penetrating tip is configured such that an inner groove is provided at a location inside a pointed end thereof, and an outer protrusion is provided on a protruding piece of the cover rod, so the penetrating tip is fixedly inserted into a lower portion of the cover rod by engagement of the inner groove and the outer protrusion.

* * * * *